US008768474B1

(12) United States Patent
Thompson et al.

(10) Patent No.: US 8,768,474 B1
(45) Date of Patent: Jul. 1, 2014

(54) ELECTRO-THERAPEUTIC STIMULATION

(75) Inventors: Denis E. Thompson, Lakeville, MN (US); Franklin Williard Schroeder, Jr., Lakeville, MN (US)

(73) Assignee: ARP Wave LLC, Apple Valley, MN (US)

( * ) Notice: Subject to any disclaimer, the term of this patent is extended or adjusted under 35 U.S.C. 154(b) by 693 days.

(21) Appl. No.: 12/898,333

(22) Filed: Oct. 5, 2010

Related U.S. Application Data

(60) Provisional application No. 61/248,694, filed on Oct. 5, 2009.

(51) Int. Cl.
*A61N 1/36* (2006.01)
(52) U.S. Cl.
USPC ............................................. 607/48; 607/49
(58) Field of Classification Search
CPC .......... A61N 1/36003; A61N 1/36171; A61N 1/36175; A61N 1/36014; A61N 1/0452
USPC ...................... 600/546; 607/48, 49
See application file for complete search history.

(56) References Cited

U.S. PATENT DOCUMENTS

| | | | |
|---|---|---|---|
| 2,532,788 A | 12/1950 | Sarnoff | |
| 2,771,554 A | 11/1956 | Gratzl | |
| 3,640,284 A | 2/1972 | De Langis | |
| 3,833,005 A | 9/1974 | Wingrove | |
| 3,908,669 A | 9/1975 | Mau et al. | |
| 4,019,519 A | 4/1977 | Geerling | |
| 4,071,033 A | 1/1978 | Nawracaj et al. | |
| 4,121,594 A | 10/1978 | Miller et al. | |
| 4,153,061 A | 5/1979 | Nemec | |
| 4,305,402 A | 12/1981 | Katims | |
| 4,315,503 A | 2/1982 | Ryabi et al. | |
| 4,374,524 A | 2/1983 | Hudek et al. | |
| 4,392,496 A | 7/1983 | Stanton | |
| 4,505,275 A | 3/1985 | Chen | |
| 4,535,777 A | 8/1985 | Castel | |
| 4,556,051 A | 12/1985 | Maurer | |
| 4,580,570 A | 4/1986 | Sarrell et al. | |
| 4,690,145 A | 9/1987 | King-Smith et al. | |
| 4,719,922 A | 1/1988 | Padjen et al. | |
| 4,763,656 A | 8/1988 | Nauman | |
| 4,850,357 A | 7/1989 | Bach, Jr. | |
| 5,107,835 A | 4/1992 | Thomas | |
| 5,109,846 A | 5/1992 | Thomas | |
| 5,109,848 A | 5/1992 | Thomas et al. | |
| 5,841,866 A | 11/1998 | Bruwer et al. | |
| 6,507,757 B1 * | 1/2003 | Swain et al. | 607/49 |
| 6,584,358 B2 | 6/2003 | Carter et al. | |
| 7,519,427 B2 * | 4/2009 | Sakagami et al. | 607/43 |
| 2006/0085049 A1 * | 4/2006 | Cory et al. | 607/48 |
| 2012/0041513 A1 * | 2/2012 | Tucker et al. | 607/48 |

OTHER PUBLICATIONS

ARP Manufacturing, LLC, Ride the Wave, Arpwave, powered muscle stimulator operation guide, Sep. 18, 2007.

* cited by examiner

*Primary Examiner* — Tammie K Heller
(74) *Attorney, Agent, or Firm* — Shewchuk IP Services, LLC; Jeffrey D. Shewchuk

(57) ABSTRACT

A method of electro-therapeutic stimulation uses an electrical signal with a periodic-exponential background pulse over a controllable periodic-exponential main pulse. By properly setting the signal and moving electrodes to proper locations on the body, the signal is used to electro-therapeutically mimic a cross-crawl pattern and return a patient to a state of neurological balance, to identify specific cellular disruption locations, to treat the identified cellular disruption locations including performing a pain associated movement, and to neurologically train from a facilitator muscle to one or more receiver muscles.

24 Claims, 7 Drawing Sheets

ELECTRO-THERAPEUTIC STIMULATION

CROSS-REFERENCE TO RELATED APPLICATION(S)

This application claims priority from Provisional Application No. 61/248,694, filed Oct. 5, 2009, entitled ELECTRO-THERAPEUTIC STIMULATION.

BACKGROUND OF THE INVENTION

The present invention improves upon the apparatus and methods of U.S. Pat. Nos. 5,107,835 and 5,109,848, both of which are incorporated by reference. The ornamental appearance of one version of practicing the present invention is described in U.S. Pat. No. D603,971, incorporated by reference.

It has long been known that the neurological system operates significantly based on electrical impulses. The neurological system works in two directions, both transmitting feeling sensation and pain to the brain, and in firing muscles responsive to impulses from the brain.

It has also long been known that non-biological sources of electrical stimulation can be used to control certain muscles. For instance, the pacemaker works on this principle. Transcutaneous electrical stimulation has also been used in a variety of devices. In most applications, the placement of the electrodes and the electrical signal applied are pre-selected based upon a desired result. The apparatus and methods of U.S. Pat. Nos. 5,107,835 and 5,109,848 operate in this way, using a particular dual periodic-exponential signal form. The periodic-exponential signal form more closely resembles the exponential character of the patient's natural signals. The dual nature of the signal form allows one periodic-exponential signal suitable for sensory stimulation, and a second period-exponential signal suitable for muscle stimulation. In the device of U.S. Pat. Nos. 5,107,835 and 5,109,848, separate rheostat controls enabled a) amplitude control over the muscle stimulation waveform; b) frequency control over primary pulse of the muscle stimulation waveform; and c) control over the "on" portion of the duty cycle of the muscle stimulation waveform. While the device and methods of U.S. Pat. Nos. 5,107,835 and 5,109,848 provided many beneficial results, they did not enable full utilization of the potential for electro-therapeutic stimulation using the dual periodic-exponential signal form. The present invention is directed to methods of using periodic-exponential signal forms which were not previously known or possible.

BRIEF SUMMARY OF THE INVENTION

The present invention is a method of electro-therapeutic stimulation. An electrical signal is applied to a patient, which has a periodic-exponential background pulse over a controllable periodic-exponential main pulse. In one aspect, the signal is used to electro-therapeutically mimic a cross-crawl pattern and return a patient to a state of neurological balance. In another aspect, specific cellular disruption locations are diagnosed or identified based upon feedback provided when the dual periodic-exponential signal is applied at differing locations on the patient's body. The identified cellular disruption locations are then treated with the dual periodic-exponential signal, which may involve firstly recognizing a compensation pattern and secondly performing a movement both under certain forms of the dual periodic-exponential signal. In another aspect, training is performed by properly applying certain forms of the dual periodic-exponential signal so as to neurologically train from a facilitator muscle to one or more receiver muscles.

Figure 1:
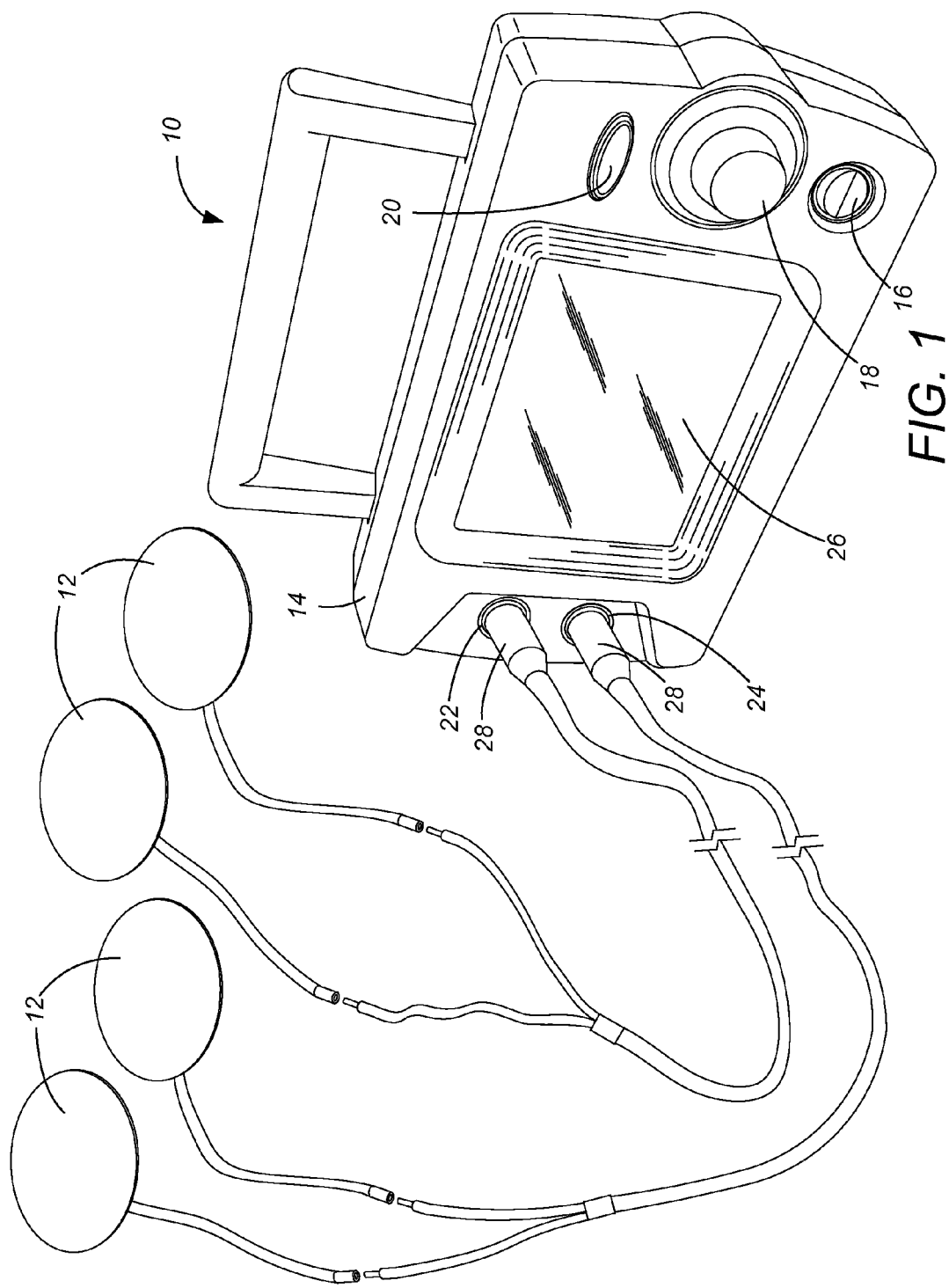
FIG. 1 is a perspective view showing the preferred electro-therapeutic stimulator for use in the present invention.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

The present invention involves methods made possible with an electro-therapeutic stimulator 10 providing tunable, reproducible waveform control of a dual periodic-exponential signal form applied to a patient through electrode pads 12. In the preferred form, the electro-therapeutic stimulator 10 has a housing 14 with an on/off switch 16, an output power dial 18, a power reset switch 20, a left output jack 22, a right output jack 24, and a touch/display screen 26. The electro-therapeutic stimulator 10 may be powered either through a standard electrical power plug (120/240 volts, 50/60 Hz AC input power, not shown), or via a battery such as a lithium ion 15 VDC battery. The left and right output jacks 22, 24 each receive a plug 28 for a pair of electrodes 12 (typically one black or negative and the other red or positive) as known in the electro-therapeutic stimulator art. Preferred electrodes 12 are intended to achieve the greatest degree of muscle penetration with the signal, such as electrode pads in excess of one inch in diameter, and more preferably about two inches in diameter, or rectangular pads of around three square inches. The electrode pads 12 can have features based upon their intended use for any given protocol, such as a tacky or pressure-sensitive adhesive layer if the protocol keeps the electrode 12 stationary, or a smoother, less-sticky electrode 12 for protocols requiring moving the electrode 12 across the patient's skin.

A general description of a dual periodic-exponential signal form is provided in U.S. Pat. Nos. 5,107,835 and 5,109,848 and is shown with reference to FIGS. 2 and 3. More detail regarding the exact electrical profile of the preferred dual periodic-exponential signal form is provided in U.S. patent application Ser. No. 12/898,520, filed on even date herewith and incorporated by reference. The dual periodic-exponential signal form has a background pulse 30 coupled onto a main pulse 32. The background pulse 30 is at a frequency to stimulate the sensory nerves of the patient, namely, at a frequency over 1 kilohertz and preferably in the range of about 1 to 1000 kilohertz, with the preferred frequency of the background pulse 30 in the range of 8 to 12 kilohertz and the most preferred background pulse 30 at 10 kilohertz. At a background pulse 30 of 10 kHz, each background pulse 30 has a period $\Delta t1$ of 100 µs. The background pulse 30 can be a sine wave, but more preferably has a characteristic RC charge/discharge or "exponential" spike shape. Within this exponential spike shape of the background signal, the preferred background pulse 30 has a power delivery duration of about 25 µs or less, with the background pulse voltage being insignificant over the remaining duration (preferably 75 µs or more) until the next background pulse 30. As explained further in U.S. Pat. Nos. 5,107,835 and 5,109,848, this background pulse 30 is intended to reproduce a portion of the patient's natural neurological signals. The frequency could be adjusted to match the sensed frequency of a particular individual's natural neurological signals; however, the background pulse frequency of 10 kilohertz has been found effective on a wide variety of people. Thus the preferred electro-therapeutic stimulator 10 is designed with a background pulse frequency of 10 kilohertz and avoids the hardware/firmware expense of designing in controls which could be added to allow the operator to control background pulse frequency.

Figure 2:
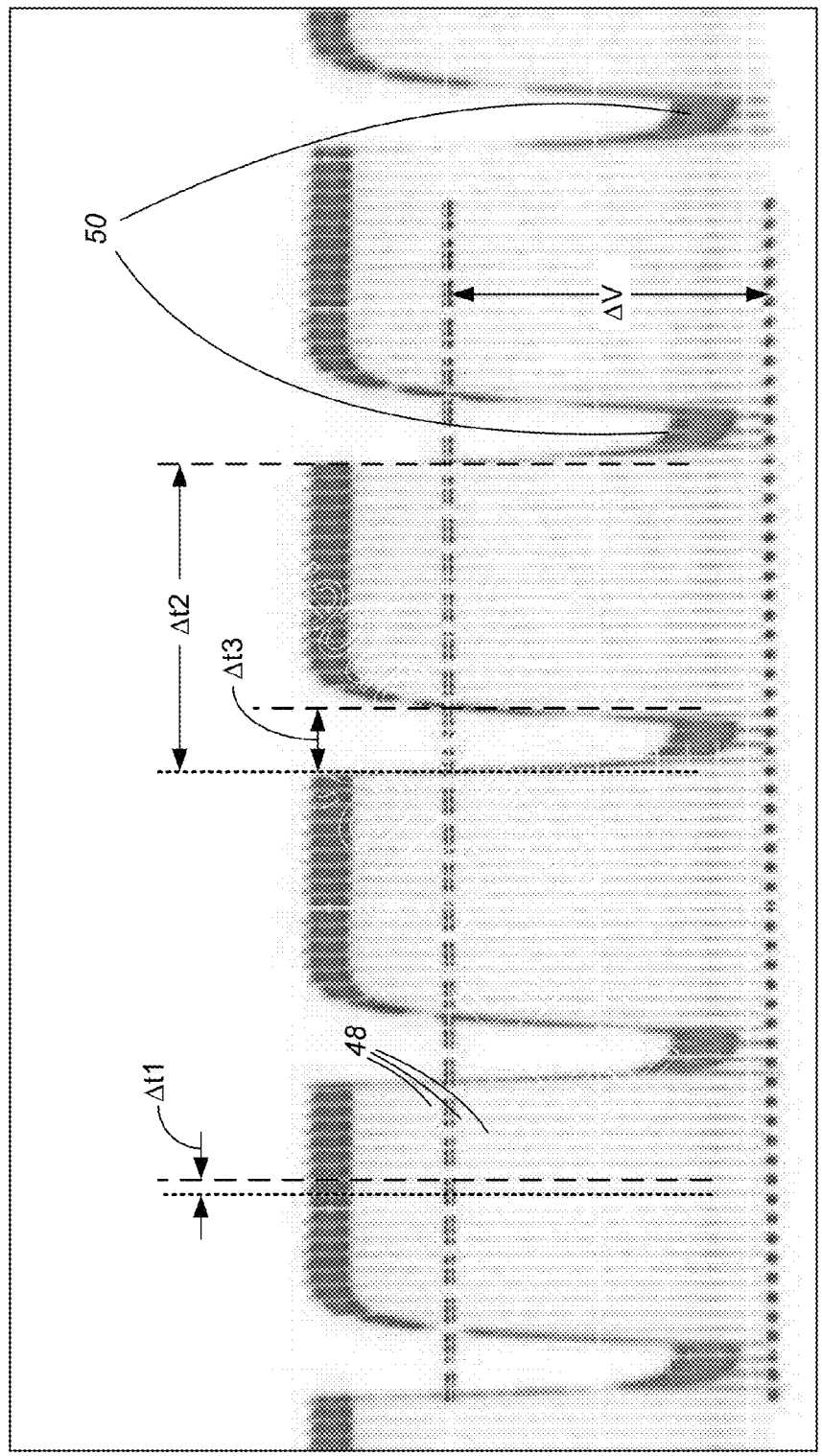
FIG. 2 is an inverted oscilloscope output of a preferred 462 pps, full power signal from the electro-therapeutic stimulator of FIG. 1 under no load.
Figure 3:
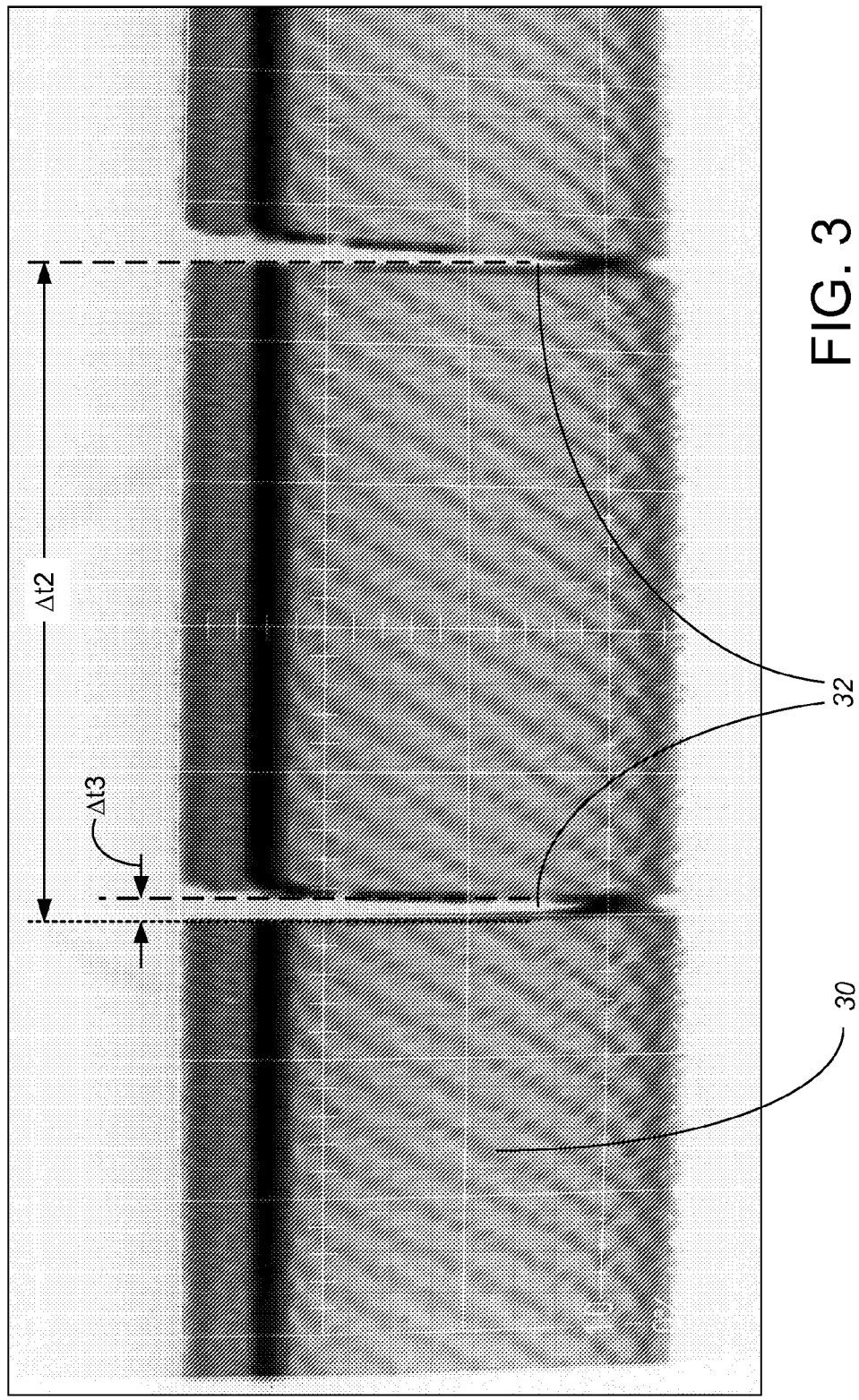
FIG. 3 is an inverted oscilloscope output of a preferred 90 pps, full power signal from the electro-therapeutic stimulator of FIG. 1 under no load.

The main pulse 32 is at a frequency to stimulate the muscles of the patient, namely, in the range of about 1 to 1000 pulses per second, (1 to 1000 hertz or pps), with the preferred frequency of the main pulse 32 being controllable by the operator within the range of 10 to 500 pps, at a preferred control granularity of 1 pulse per second. In the signal shown in FIG. 2, the main pulse 32 is shown as provided at about 482 pps. At a main pulse 32 of 482 pps shown in FIG. 2, each main pulse 32 has a period $\Delta t2$ of just over 2 ms, i.e., about twenty-one background pulses 30 for each main pulse 32. In FIG. 3, the main pulse 32 is shown as provided at about 90 pps. At a main pulse 32 of 90 pps, each main pulse 32 has a period $\Delta t2$ of just over 11 ms, i.e., about 110 background pulses 30 for each main pulse 32. When shown at 90 pps (FIG. 3), the harmonics established in the preferred signal by the preferred electro-therapeutic stimulator 10 as visible as the sine wave looking brighter and darker portions of the background signal. The main pulse 32 also has a characteristic RC charge/discharge or "exponential" spike shape. Within this exponential spike shape of the main pulse signal, the power delivery duration $\Delta t3$ of the main pulse 32 is within the range of 100 to 1000 µs (about 426 µs shown in FIG. 2), with preferred values for main pulse power delivery durations being 460 to 480 µs or alternatively about 320 µs. In general, wider signals (both main pulse 32 and background pulse 30) provide more electrical power to a greater depth of muscle penetration, which can be important for certain protocols as described herein, either for total power delivered or for a relative proportion of background pulse power to main pulse power.

The power level of the main pulse 32 is operator variable using the output power dial 18 with at least ten power level increments, and more preferably with eighteen power level increments, and more preferably with at least 100 power level increments, with the most preferred electro-therapeutic stimulator 10 having 1000 power level increments on a scale of 1 to 100. Additional granularity in the power level control adds cost to the design of the electro-therapeutic stimulator 10, and the higher granularity of power control may not be necessary for performing all protocols. When power of the main pulse 32 is delivered to a patient during an application, the power output of the preferred electro-therapeutic stimulator 10 varies nonlinearly in proportion to the load impedance presented by the body of the patient between the two electrode locations. With the preferred electro-therapeutic stimulator 10, for instance, a patient load resistance of 500 Ohms provides a full power output voltage of 31 Vrms, a patient load resistance of 2 kOhms provides a full power output voltage of 49 Vrms, and a patient load resistance of 10 kOhms provides a full power output voltage of 62 Vrms. The signals shown in FIGS. 2 and 3 are at no load, with the measured $\Delta V$ in FIG. 2, to give some indication of scale, of 108V.

The preferred electro-therapeutic stimulator 10 allows reversal of polarity, such that the black electrode pad 12 as normally wired will be negative and the red electrode pad 12 as normally wired will be positive. However, unless noted as using "reverse polarity", the methods of the present invention either do not matter as to polarity or should be run using normal polarity.

The preferred electro-therapeutic stimulator 10 allows control over balance between the right and left set of electrodes 12. For instance, the preferred embodiment allows control over the balance over a range of 0/100 to 100/0, at a granularity of 1% increases/decreases to the right and left channels. Of course, because the electrodes 12 are mobile and can be placed anywhere on the patient's body, the "right" and "left" labels can be misnomers other than designating two distinct and controllable channels. The preferred electro-therapeutic stimulator 10 allows control over duty cycle for the main pulse 32. For instance, the preferred embodiment allows control over the duty cycle over an on range of 1 to 20 seconds and over an off range of 0 to 20 seconds, with a granularity over both the on time and the off time during the duty cycle of 1 second. In one preferred embodiment, with an "off" cycle of 6 seconds or more, there is a three second ramp up to the full power for the "on" duration, and a three second ramp down to zero main pulse power during the "off" duration of the duty cycle. In a more preferred embodiment, there is no associated ramp up and ramp down of the power with any "off" duration, with the main pulse 32 delivered as an overall square wave (for instance, at 90 pps and an "on" duration of 1 second, 90 full power main pulses will be delivered during the on duration, with no partial power main pulses either immediately before or after the "on" cycle). In an even more preferred embodiment of electro-therapeutic stimulator 10 as noted below, the duty cycle allows a faster full power main pulse 32 without a ramp, such as providing the main pulse 32 at a ¼ second on and 1 second off. Each of the main pulse frequency, the balance and the duty cycle levels are fully and exactly reproducible, to a digital, numeric value, with the touch screen control.

The methods of the present invention involve protocols to produce surprisingly beneficial results in terms of application to a specific condition being suffered by a specific patient. During application of the waveform to the patient, feedback is taken from the patient which is used to gauge the effectiveness of the waveform. Through this feedback, the waveform is tuned to better treat the patient's condition. Preferred feedback mechanisms include monitoring the patient's heart rate, monitoring the patient's respiratory rate; visual inspection of muscle firings (including large and small movements) on the patient's body, and pain or physical sensation feedback given (typically verbally) from the patient.

The methods of the present invention will be described with four different purposes, namely a first set of protocols to achieve neurologic balance, a second set of protocols to identify specific cellular disruption locations, a third set of protocols to provide treatment to identified cellular disruption locations, and a fourth set of protocols to achieve training of muscles or muscle groups. To the extent not clear from the discussion, the term "set of protocols" is intended to indicate that many of the specifics described can be modified—sometimes slightly and sometimes to a great degree—while still using the concepts and methodology of the present invention.

Neurologic Balancing

The neurologic balancing protocols are only necessary for patients who are not initially in a state of neurological balance. Unfortunately, the majority of patients (having pain either on a daily basis or associated with a particular movement) are not initially in a state of neurological balance, which contributes to the reason they are seeking treatment in the first place. The neurologic balancing protocols can be analogized to the adjustments to a patient's back performed by a qualified and skilled chiropractor. As known in the art of chiropracty, often pains in one location on the patient's body are merely a symptom of a neurological problem in another location on the patient's body. For instance, many knee, hip, shoulder and neck pains have a root cause due to an alignment or "imbalance" problem in the patient's back, which neurological imbalance itself may have been caused by a different root muscular problem, such as a repeated unnatural muscular stress, poor posture, etc. Thus, while the present invention can be used to treat numerous pains or injuries of the patient, often a first step before diagnosis or treatment is a neurological balancing step.

For better understanding of the concept of "neurologic balance" as discussed herein, one method to determine a state of neurologic balance involves the strength of resistance of a patient's hip flexor muscles with a flex in the patient's back vertebrae. The patient is placed in a supine position, with legs extended, and asked the raise one leg and foot upward while performing a dorsal flex of the ankle (i.e., the opposite of pointing one's toes). The therapist then pushes downward (against the hip flexor) on the patient's leg and notes the amount of strength with which the patient can resist the downward force on his or her leg. This is preferably repeated for both legs. Next, the patient is asked to perform the same exercise while arching his or her lower back to the greatest extent possible. A patient with a common neurological imbalance (located in their lower back) will exhibit a marked decrease in ability to resist the downward force in the arched back position. A patient with neurological balance will exhibit considerable strength retention in ability to resist the downward force in the arched back position.

To achieve the best results from the electro-therapeutic stimulation, a first step is to place a patient in a state of neurological balance. As noted above, prior art methods of placing a patient in neurological balance are practiced by chiropractors, but one aspect of the present invention is a set of protocols to place the patient in neurological balance through electro-therapeutic stimulation. The exact neurological balancing protocol used for any patient can vary based upon numerous factors, with a primary factor being the observed location of neurological imbalance. With a common neurological imbalance being a lack of proper alignment of the L4 and/or L5 vertebrae, the common electro-therapeutic protocol described herein is used to adjust the patient's L4 and/or L5 vertebrae.

To adjust the patient's L4 and/or L5 vertebrae, the concept applied is to return those vertebrae to a previous condition wherein they were not out of alignment. Unfortunately, it may be difficult or impossible to quickly determine when the alignment problem began. For some patients, the alignment problem may have been a relatively recent event. Other patients may have lived with the alignment problem for years or decades, perhaps without knowing that their L4 and/or L5 vertebrae were out of balance for the whole duration. However, it is assumed that early neurological connections in the patient's brain were properly made in childhood as part of what is known as the "cross crawl pattern", in which as the right arm goes forward, the left leg does as well, and vice versa. In this aspect and when applied to out of balance L4 and/or L5 vertebrae, the present invention attempts to use electro-therapeutic stimulation using the preferred stimulator 10 to gently reproduce the proper cross-crawl patterning across these vertebrae.

Figure 4:
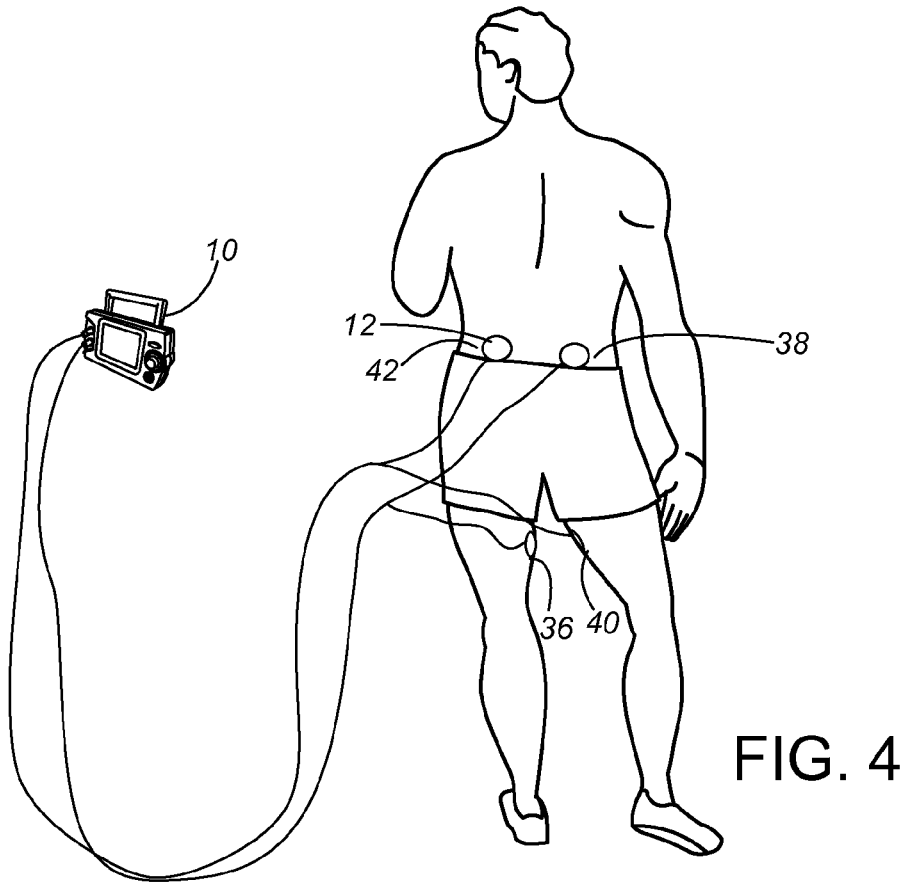
FIG. 4 is a drawing of a patient receiving electro-therapeutic treatment in accordance with one or more protocols of the present invention.
Figure 5:
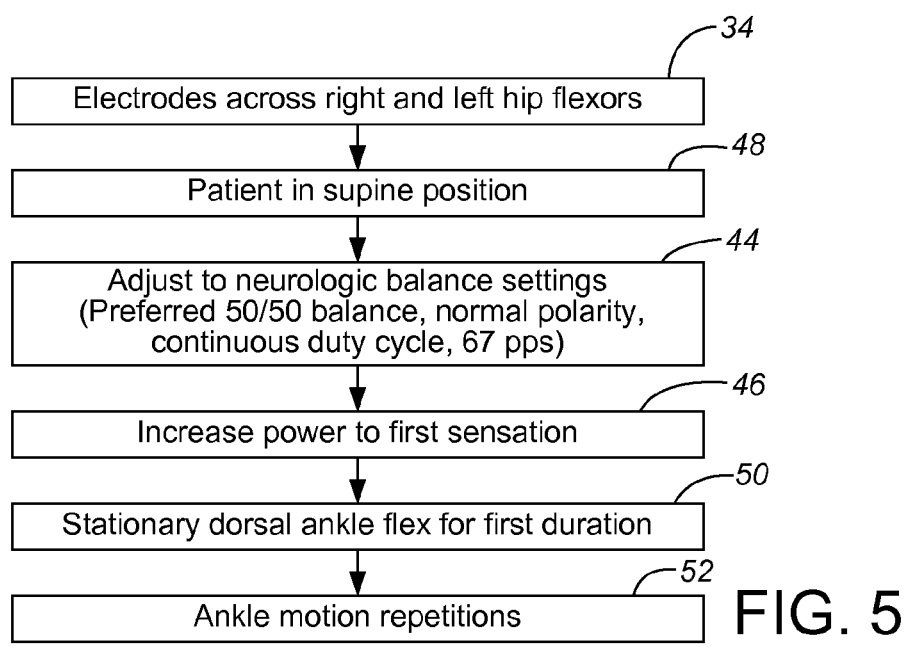
FIG. 5 is a flow chart summarizing steps of a set of neurological balancing protocols of the present invention.

In more practical terms shown generally in FIGS. 4 and 5, the electro-therapeutic neurological balancing mimicking cross-crawl patterning is performed by placing 34 the electrodes 12 of the electro-therapeutic stimulator 10 across the patient's hip flexors. On the first channel, a black electrode 12 is placed on the patient's inner left thigh 36, adjacent the terminal end of the left hip flexor. The corresponding first channel red electrode 12 is placed on the patient's lower right back 38, generally adjacent the opposing end of the left hip flexor, i.e., at the insertion of the iliopsoas opposite the left hip flexor. The second channel electrodes 12 are placed in corresponding opposing locations, i.e., with the black electrode 12 placed on the patient's inner right thigh 40 adjacent the terminal end of the right hip flexor and the red electrode 12 on the patient's lower left back 42 adjacent the insertion of the iliopsoas. The signal is adjusted 44 to neurological balance settings, such as balancing the two channels at 50/50, with polarity normal, with a duty cycle at continuous, e.g., 1 on and 0 off. The frequency of the main pulse 32 is selected between 40 and 100 pps, with a preferred selected 65-69 pps to provide the desired stimulus. The power level for electro-therapeutic neurological balancing mimicking cross-crawl patterning could be at any power over a wide range, but it has been found that a minimal amount of power can be used to obtain beneficial results. Thus, the power setting can be started at 0 and increased 46 until feedback from the patient (preferably oral feedback) indicates that the sensation from the electro-therapeutic stimulation is first felt. In a supine position 48 (the patient in FIG. 4 is shown standing during application of the electrodes, after which he is asked to lay down), legs extended but relaxed with heels together and with a dorsal flex of the ankle, a stationary position is maintained 50 during the electro-therapeutic stimulation for a short period, such as a duration of 10-600 seconds, and preferably a duration of about 30 seconds. The patient is then asked to perform a number of repetitions 52 of ankle extensions and flexes during continued electro-therapeutic stimulation without changing signal settings. The preferred number of repetitions is 5, but a greater number can alternatively be used, or possibly a lower number of repetitions for some patients.

This simple electro-therapeutic stimulation protocol has been found quite effective at improving neurological balancing for patients who initially demonstrate a lack of proper alignment of the L4 and/or L5 vertebrae, but the concept can be applied more broadly. That is, for any patient who initially demonstrates a lack of neurological balance at a given location (in the given example, the L4 and/or L5 vertebrae), consideration should be given to determine an earlier state of neurological balance at that location wherein the patient first learned coordinated, balanced movement (in the given example, the cross-crawl pattern). The electro-therapeutic stimulator 10 should then be used across the primary muscles associated with that early coordinated, balanced movement (in the given example, the hip flexors), which should be given electro-therapeutic stimulation first in a stationary position to relax those muscles and then through a number of repetitions of further coordinated movement (in the given example, ankle movements).

This aspect of the invention has quickly obviated many obstacles associated with prior art methods. Firstly, the vast majority of prior art electrical stimulations were performed with a completely different signal, which does not provide the benefits of the present invention. Secondly, the vast majority of prior art electrical stimulations did not adequately consider neurological rather than merely musculature effects of the signal. Very few therapists have recognized the importance of neurological balancing in obtaining electro-therapeutic benefits. For those few therapists who may have recognized the importance of neurological balancing, the prior art often involved sending the patient to a chiropractor prior to continuing with electro-therapeutic stimulation. Further, this set of protocols is very beneficial for a wide range of patients, well tolerated and with little discomfort.

Diagnosis/Identifying Specific Cellular Disruption Locations.

Once the patient is in neurological balance so signals through the patient's nervous system are flowing freely, the next set of protocols seeks to diagnose or identify locations of muscular cellular disruption. Soft tissue damage such as ligament and tendon damage most commonly occurs because the muscles at that location on the body did not fire at proper timing, sequence or strength to absorb the force across that location, which force was then transferred to the ligament or tendon rather than absorbed by the muscle. Similarly, joint pain commonly occurs because the muscles are not firing at proper timing, sequence or strength to absorb the force across the joint during a particular movement. Often the improper muscle firing is due, at least in part, to a compensation pattern the patient has established rather than perform a particular movement with proper fluidity and balance. The diagnostic protocols and the subsequent treatment protocols are designed to address the root cause and resulting compensation pattern, so a particular movement or set of movements can occur pain-free.

Figures 6A, 6B:
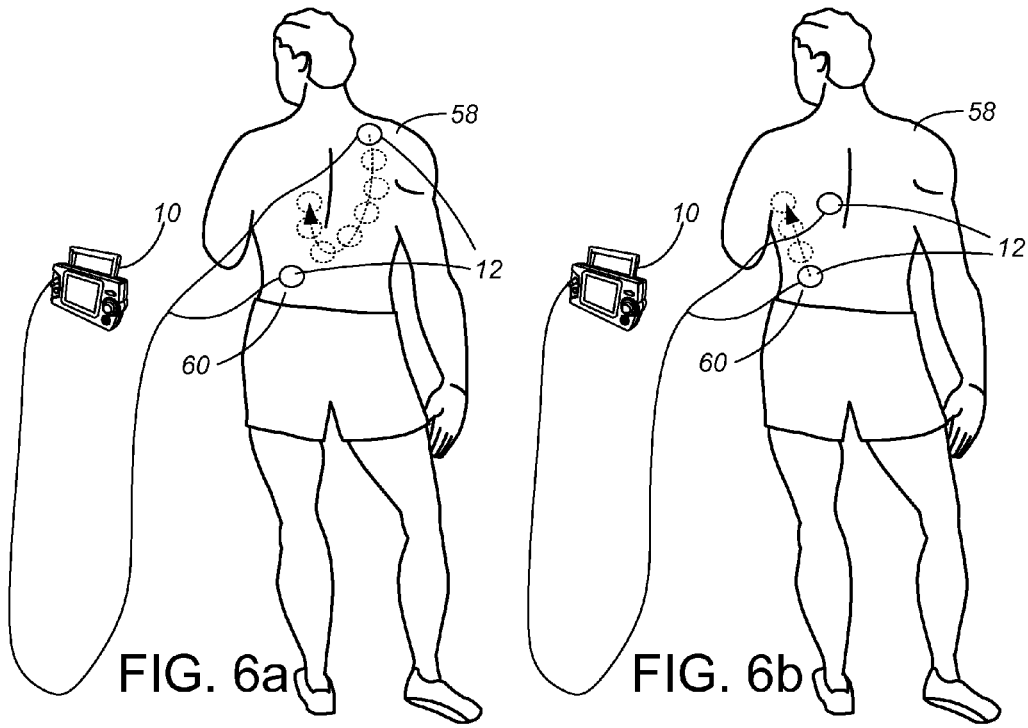
FIGS. 6a and 6b are drawings of a patient undergoing electro-therapeutic diagnosis of muscle cell disruption locations in accordance with one or more protocols of the present invention.
Figure 7:
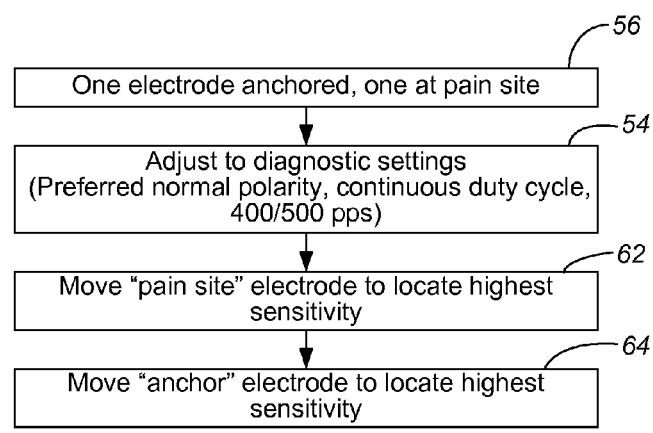
FIG. 7 is a flow chart summarizing steps of a set of diagnostic protocols of the present invention to identify cellular disruption locations.

The electro-therapeutic signal is applied and used in a diagnostic mode 54, shown with reference to FIGS. 6a, 6b and 7, to identify the most beneficial placement of the electrodes 12 for a subsequent treatment. A preferred diagnostic mode begins with the application of a relatively low amplitude, high frequency main pulse signal on a single channel. For instance, the diagnostic mode 54 may include a main pulse signal in the range of 400 to 500 pps and preferably at 400 pps for a high power diagnosis and at 500 pps for a low power diagnosis. As a single channel protocol, the balance may be placed entirely on the channel being used. Polarity is generally unimportant at this stage, and a continuous duty cycle at continuous, e.g., 1 on and 0 off, may be used. The power setting for the diagnosis depends upon the patient's comfort level and the clarity of results being obtained. For a high power diagnosis, the power setting may be at full power, while for a low power diagnosis the power setting may be dialed beneath the power of first sensation, including only a background signal and zero power on the primary pulse.

The diagnostic signal is transcutaneously applied using relative large electrodes 12 to large muscles in the vicinity of trauma identified by a patient. For instance, for a patient complaining of knee problems, the electrodes 12 may be positioned across the calf just below the knee and hand-held firmly onto the patient's skin. For a patient complaining of shoulder problems (shown in FIG. 6a), one electrode 12 (black) may be positioned 56 on the shoulder 58 and the other electrode 12 (red) anchored on the lower back 60 at the patient's latissimus dorsi base adjacent the lumbar triangle opposite the first electrode 12 (e.g., right shoulder and left lumbar triangle). As current generated by the preferred electro-therapeutic stimulator 10 is somewhat dependent upon load resistance, a high power diagnosis signal might provide a peak amplitude of about 5-8 mA (10-30 V). One of the electrodes 12 (preferably the electrode 12 closest the pain site) is then slowly moved 62 around the musculature structure in a direction back toward the spinal column, while the patient is questioned regarding either pain sensitivity (high power diagnosis) or any sensation of feeling (low power diagnosis) from the applied signal.

For low power diagnosis, a significant depth of muscle penetration of the background signal 30 is particularly important. The electro-therapeutic stimulator 10 described in copending application Ser. No. 12/898,520 of Thomas et al., entitled "ELECTRO-THERAPEUTIC STIMULATOR" and filed on even date herewith, is particularly important in obtaining greater depth of muscle penetration with the background signal 30, and is incorporated herein by reference. Generally speaking, prior art background pulses did not achieve sufficient depth of muscle penetration to make this low power diagnosis method possible. Without a significant depth of muscle penetration, the patient would not be able to feel the background pulse 30 by itself even if the electrodes were positioned on opposite sides of a cellular disruption location. By increasing the depth of background pulse penetration, the present invention allows diagnosis of the cellular disruption location at the threshold of first sensation (i.e., the patient identifies when the sensation—due to the background pulse 30—is first mildly felt) rather than at a pain threshold (i.e., rather than where the patient identifies which location hurts most acutely due to the main pulse 32).

For most conditions, this diagnostic electrode movement is used to identify the electrode location of greatest sensitivity to the diagnostic signal. For the low power diagnosis, the diagnostic electrode movement is particularly used to locate a cellular disruption end point where the sensation associated with the background pulse 30 is maximized. Commonly the electrode location of greatest sensitivity to the diagnostic signal will not be the location of pain felt by the patient, but will be one or several muscle locations different from the pain location. A muscle irregularity (cellular disruption) in one location on the body, such as a muscle-firing problem, a muscular sodium channel leakage or potassium channel leakage problem, or a muscle scar-tissue problem, will often manifest itself in pain felt in a different location on the body. Knee pain can be caused by less-than-optimal ankle or calf muscles, by less-than-optimal thigh muscles, by less-than-optimal hip muscles, etc. The important diagnostic issue is to find the location of the muscle weakness or irregularity (cellular disruption), which is often different from the location of pain felt on a day-to-day basis.

After one or several cellular disruption locations are identified, the other (initially "anchor") electrode 12 is moved 64 around the identified muscle locations as shown in FIG. 6b to locate the opposing cellular disruption end point. The electro-therapeutic signal should be kept the same during this second half of the diagnosis procedure, i.e., with the low power diagnosis looking for the greatest sensitivity to the background signal and the high power diagnosis looking for the greatest sensitivity to the main pulse signal.

It should be understood that the electro-therapeutic signal travels three-dimensionally through the patient's tissue, i.e, not in a single, narrowly defined direct path but rather spreading itself out in the tissue that is in between and adjacent to the two electrodes 12. The greatest sensation is based upon having the diagnostic signal travel through the entirety or as much of the cellular disruption as possible but through as little completely healthy muscle tissue as possible. The diagnostic process results not only in finding which muscle(s) or muscle group(s) shows irregularity, but also in determining the size and the orientation of the muscle irregularity within that muscle or muscle group.

Treatment Delivery to Identified Cellular Disruption Location.

Figure 8:
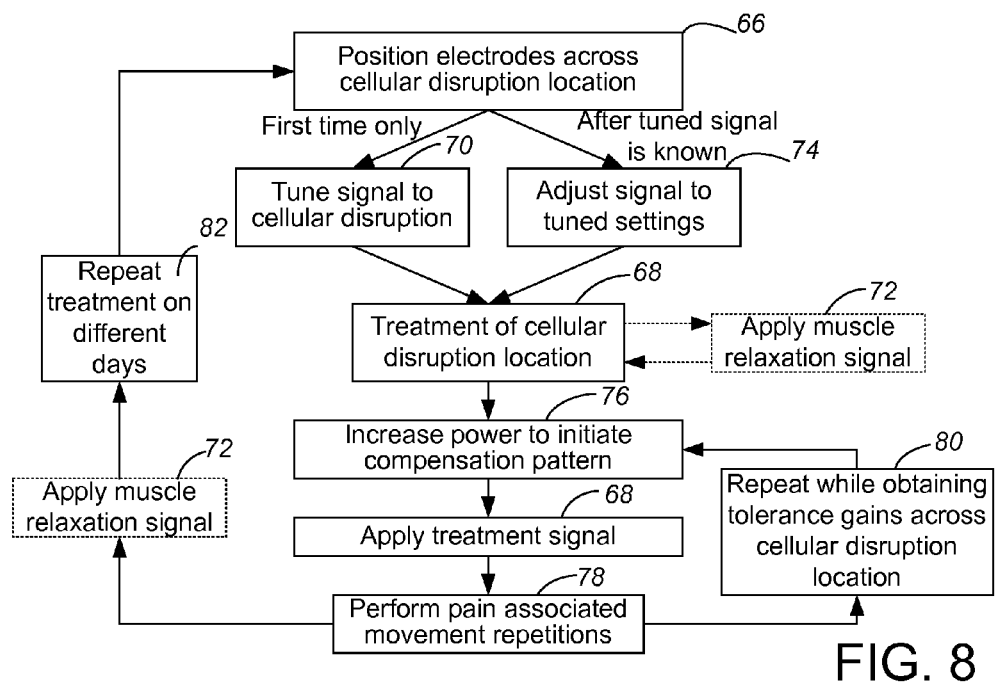
FIG. 8 is a flow chart summarizing steps of a set of treatment protocols of the present invention.

Once a location of muscle cellular disruption is identified 66, then a regimen of various therapy modes 68 can be administered based upon the identified problem, described generally with reference to FIG. 8. The therapy modes 68 include muscle relaxation (to improve flexibility), scar tissue breakdown and healing (including increasing blood flow to the irregular muscle area), muscle firing timing during a repetitive motion (training the brain to store electrical information on the proper way to perform a learned action); and muscle strengthening (protein replication within the muscle). The therapy 68 enhances neurological balance to the affected or injured muscle groups, and enhances the ability of the muscles to absorb force over the painful joint or area. The therapy 68 is particularly intended to minimize or completely avoid compensation patterns which are commonly learned in response to pain.

For instance, the electrodes 12 may be positioned 66 for enhanced healing of a cellular disruption location identified in the patient's left quadricep. Possibly due to a learned walking motion, most patients' left quadricep is neurologically coupled to the patient's right bicep. At one particular main pulse frequency (for instance, at 128 pps), possibly restricted to a specific duty cycle, power level, balance and polarity (for instance, at a 3 on/2 off, power level 8 (out of 18), 50/50 balanced, normal polarity waveform), application of the waveform to the left quadriceps will cause the patient's right bicep to responsively fire. The firing of the right bicep can be visually identified while the technician is tuning 70 the waveform, and further can be felt and identified by the patient while undergoing treatment. At a different main pulse frequency (for instance, at 243 pps, at a 5 on/10 off duty cycle, power level 5 (out of 18), normal polarity waveform), application of the waveform to the left quadriceps will cause the patient's left quadriceps to tense, but still maintain sufficient relaxation to permit knee movement. The signal must accordingly be tuned 70 to have the greatest effect for a particular patient and for a particular cellular disruption location.

For many desired treatments, the applied waveform can produce surprisingly different therapeutic results based on whether the main pulse frequency is properly tuned (at 128 pps for the first treatment) or improperly tuned (for instance, at 130 pps). Applicant theorizes that the importance of the proper tuning 70 of the waveform is based upon different electrical energy absorption rates of different tissue structures (scar tissue versus healthy tissue, for instance), possibly at a harmonic rate that exactly matches the electrical transmission rate and size of that patient's physical layout of scar and healthy tissue. The importance of the proper tuning 70 of the waveform may also be patient specific, with the neurologic or musculature response to the preferred signal form differing slightly from one patient to the next. Much like different patients may have different resting heart rates, different patients may also have differing characteristic frequencies and signal forms at which their nervous system naturally operates, with the characteristic frequencies and signal forms also possibly varying over the life span or overall health of the patient. The most beneficial application of the electronic waveform thus requires precise tuning 70 of the waveform. That is, applying the waveform at 130 pps for one particular patient may accelerate healing only slightly, while applying the waveform at 128 pps for that patient may accelerate healing significantly.

Before, after or during these treatments 70, a relaxation therapy 72 can be used to loosen and increase flexibility in the muscle. For instance, a relaxation setting 72 might be at 385 pps, at an 18 on/3 off duty cycle, power level 3 (out of 18), reverse polarity waveform). The relaxation blocks 72 in FIG. 8 are depicted in dashed line to denote that they are optional, particularly depending upon the reaction of the patient's muscle tissue to the treatment signal.

For multiple treatments, it can be very important that treatment again be provided at 128 pps. That is, not only does the fine granularity of the controls of the preferred embodiment allow proper tuning 70, but then the waveform can be quickly and easily reproduced 74 at exactly 128 pps. While the prior electrical stimulator provided dial/rheostat inputs of main pulse frequency, output power, balance and duty cycle, those dial controls were not nearly as exact as the present invention, and provided no confidence in reproducibility of the type required for the most beneficial tuning and use of the present invention. Without the fine granularity and proper tuning 70, it was impossible to realize the various protocols of different treatments which could be applied to a particular patient/particular muscle irregularity.

For many patients, the purpose of the electro-therapeutic stimulation is to address pain felt during a particular movement or set of movements (a "pain associated" movement). For instance, a patient might complain of knee pain associated with deep knee bends, or of shoulder pain associated with throwing, hitting or lifting motions. If the patient has identified a "pain associated" movement, with the pain occurring in a different location than the identified cellular disruption location, then a further aspect of the treatment process is possible. Namely, the treatment process can not only seek to directly treat 68 the cellular disruption location, but can also seek to identify and correct the patient's compensation pattern for the pain associated movement.

In order to "break" the patient's compensation pattern, the compensation pattern must first be identified. Because the therapist often does not see the exact conditions under which the pain to the patient occurs, identifying the compensation pattern typically involves using the electro-therapeutic stimulator 10 to reproduce 76 the compensation pattern. With the electrodes 12 located at ends of the identified cellular disruption location 66 and properly tuned 68, 70, the power is gradually increased 76 until the patient feels enough pain at the cellular disruption location to enter into a compensatory movement. The patient is visually watched and the compensatory movement identified. For instance, the compensatory movement will frequently involve a shifting of weight or rotation out of the strongest position for the muscle being stimulated.

When power level inducing the compensatory movement is reached, the patient is then asked to perform the "pain associated" movement 78, without turning down the power or otherwise changing the tuning of the electro-therapeutic stimulation. For instance, the patient may be asked to perform a series of knee-bends or to perform a series of throwing or hitting motions. Only a few repetitions of the "pain associated" action 78 are required, with the preferred number being 5 repetitions. In most cases, the "pain associated" action 78 will necessarily take the patient out of the compensatory movement, such as placing weight equally on both feet or performing the "pain associated" action without the rotational movement.

When properly done, the performing of several repetitions of the "pain associated" action 78 results in an increase in the patient's tolerance 80 for electro-therapeutic stimulation across the cellular disruption location. The power of the electro-therapeutic stimulation may now again be gradually increased 76 until the patient enters into a compensatory movement, at which point the patient is again asked to perform several repetitions of the "pain associated" action 78. This cycle of performing "pain associated" action 78, increasing power 76, performing "pain associated" action 78, increasing power 76, etc. can be repeated 80 several times. The purpose of this portion of the treatment protocol is to effectively disassociate the improper compensation pattern from the "pain associated" movement, returning the patient to a new homeostasis. When complete, the patient can perform the "pain associated" movement in proper form, without pain either at the cellular disruption location or in the original (knee or shoulder) pain location. This "breaking" of the compensation pattern results in firing of the muscles at proper timing and sequence to absorb the force across the joint during that particular movement.

Regardless of whether the treatment therapy 68 is performed with or without the steps 76, 78, 80 to break the compensation pattern, it is typically repeated 82 several times over several different days. Several treatments may be necessary to achieve the desired result of breaking down scar tissue and/or increasing blood flow to the cellular disruption location in the muscle and to fully break the compensation pattern so the patient can return to natural, pain free movement.

The present treatment delivery invention thus involves the recognition that a cellular disruption location can cause a compensation pattern which then in turn can cause pain in an associated movement. Instead of focusing on the symptom of the pain, the present invention focuses on treating the cause of the cellular disruption location and on breaking the compensation pattern associated with that cellular disruption location. Once the compensation pattern is broken, the patient is left free to perform the "pain associated" movement in a proper way, without pain, and without entering the compensation pattern formerly associated with that pain. Until the present invention identified that the precise tuning of the waveform (not to mention the proper waveform itself) was necessary to identify and address the compensation pattern, and until the present invention recognized that performing the pain associated movement during application of a high power treatment signal to the cellular disruption location could overcome the compensation pattern, there was no mechanism available to obtain these benefits. The present invention thus provides a set of protocols which greatly accelerate the reduction of pain and return to proper movement which was not possible with the prior art.

Electro-Therapeutic Training.

In addition to the balancing, diagnosis and treatment described above, another aspect of the present invention involves training of muscles using the preferred electro-therapeutic stimulator 10. In general terms, muscle "training" as used herein refers to improving the neurological pathway for a muscle or muscle group, which in turn results in a stronger, more efficient usage of that muscle or muscle groups.

To explain the training strategy employed with the present invention, it helps to understand the neurological coupling of muscles which naturally occurs within the human body. For the primary muscles, a first grouping of neurologically coupled muscles includes calves (plantarflexars only, i.e., gastrocnemius and soleus), quads (quadriceps femoris, though vastis mediolis doesn't really behave within this group), hip flexors (primarily the iliopsoas and adductors), lats (latissimus dorsi), biceps and forearms (wrist flexors, forearms flexors, extensors, and brachioradialis). A second grouping of neurologically coupled muscles includes hamstrings (biceps femoris), pecs (pectoralis major), triceps (triceps brachii) and the anterior tibialis. Several other muscles, including the gluts (gluteus maximus), abdominals and lower back (primarily the thoracolumbar fascia) couple fairly well with muscles out of both groups.

Within each of these muscle groupings, the muscles are neurologically coupled, with the timing of firing one muscle in the group being inherently related to the timing of firing other muscles within the group. Muscles within each group seem to share some aspects of a common neurological communication pattern. It's as if muscles within the first group learn to speak one neurological language with the brain, and muscles within the second group learn to speak a slightly different neurological language with the brain. Coordinated movement requires precisely timed tension and relaxation of different muscles. As coordination between the various muscles is practiced and improves across the lifespan of the trainee, the communicative neurological pathway coupling for each muscle or muscle group appears to become more and more ingrained.

The electro-therapeutic training aspect of the present invention involves the realization that the neurological pathway for one muscle (the "facilitator" muscle) can be used as a basis for improving the neurological pathway for another muscle (the "receiver" muscle) from the same muscle grouping, essentially improving the strength and timing of the receiver muscle and improving the coordination between the facilitator and receiver muscles. Improving the strength and coordination of various muscles within each group leads to generally improved performance at a wide variety of activities. While the present invention can be used to focus on training of a particular muscle to improve performance in a particular activity, the present invention can be beneficially employed to improve performance of all the muscles in a group up to the level of the facilitator muscle.

Figure 10:
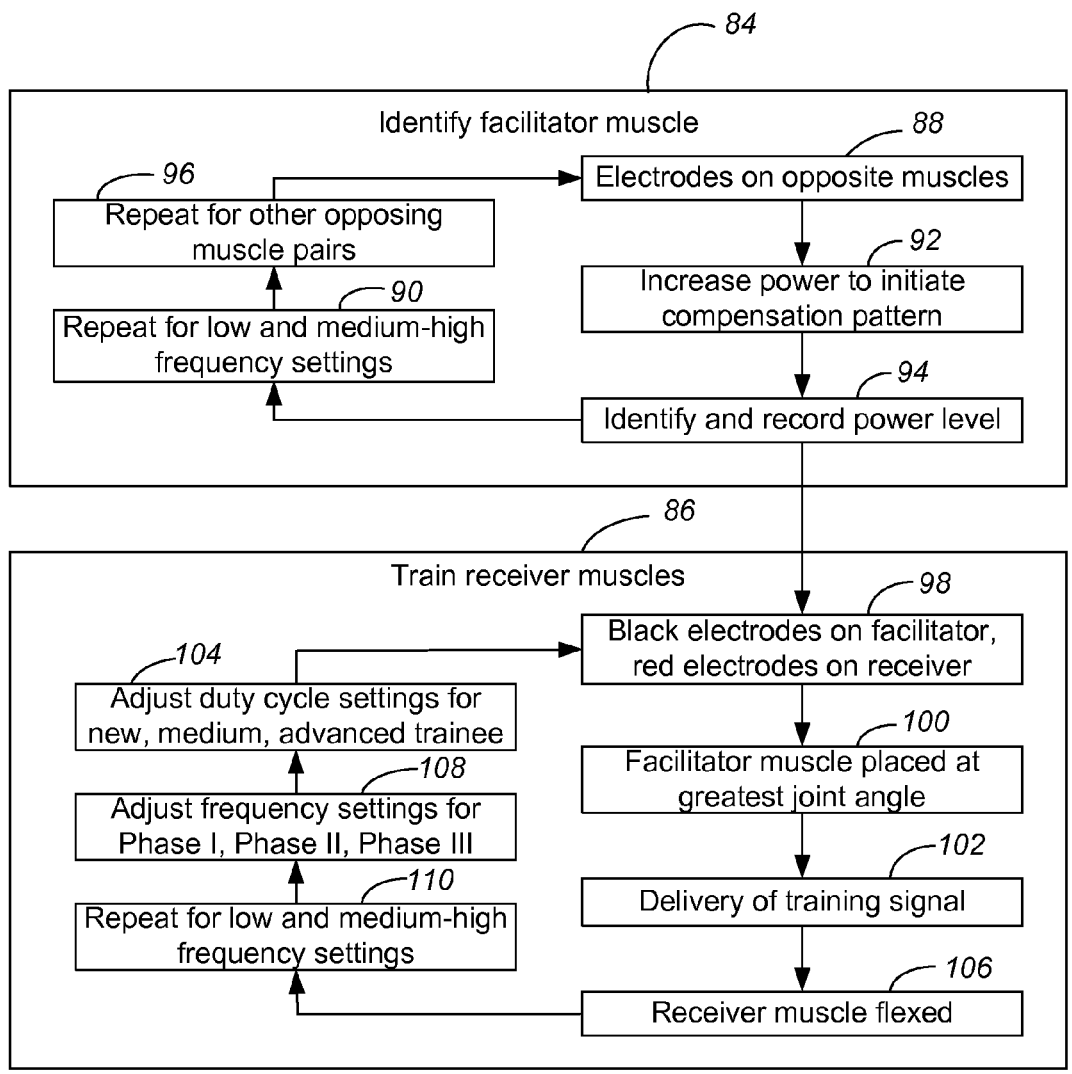
FIG. 10 is a flow chart summarizing steps of a set of training protocols of the present invention.

As broadly shown in FIG. 10, the first stage 84 of electro-therapeutic training is to identify, for any given trainee, which muscles within each group enjoy better neurological communication and should be designated as facilitator muscles, and which muscles within each group suffer worse neurological communication and should be designated as receiver muscles. Subsequently within the electro-therapeutic training, the neurological communication of the facilitator muscle is applied to the neurological communication of the receiver muscles, teaching or "training" 86 the receiver muscles how to respond to signals from the brain more like the facilitator muscle, and thus turn on and turn off faster responsive to signals from the brain.

Figure 9:
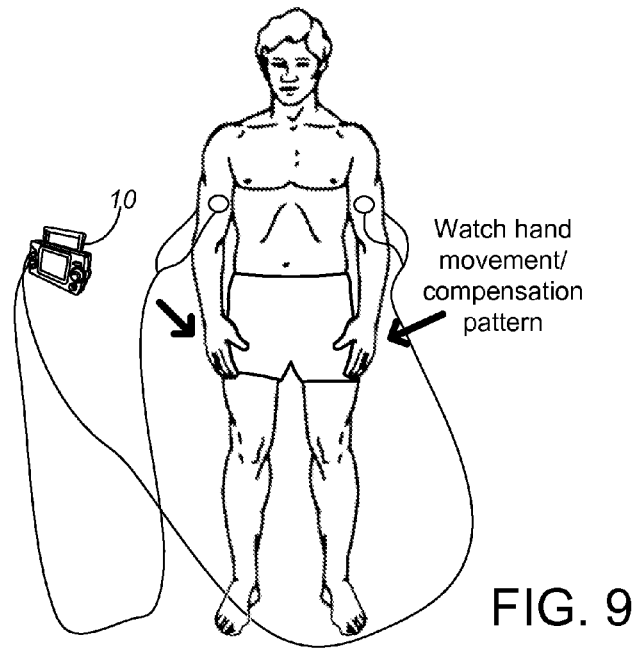
FIG. 9 is a drawing of a trainee undergoing a first step of electro-therapeutic identification of facilitator muscles.

Additional detail is provided with reference to FIGS. 9 and 10. For instance, identification of the facilitator muscle 84 in its preferred form involves using the preferred electro-therapeutic stimulator 10 to apply a quantifying test to the trainee. The preferred quantifying test starts by applying 88 a first electrode on a given channel to one muscle out of one of the groups, in this example the trainee's right bicep. The opposite electrode is placed 88 on the trainee's opposing muscle from the other group, in this case the right tricep. Equivalent electrode locations can be also used on the left bicep and tricep.

The settings for the electro-therapeutic stimulator 10 for this quantifying test include a duty cycle which is partially on and partially off, such as a duty cycle of ¼ second on, 1 second off, for which polarity doesn't matter. For best results, the quantifying test is performed 90 at two different frequencies, both a low frequency and a mid-to-high frequency. For instance, the low frequency quantifying test may be performed at 40 pps, or more preferebly may be performed at 10 pps if the electro-therapeutic stimulator has a 10 pps setting. The mid-to-high frequency quantifying test may be performed at 245 pps.

At these settings, the power is gradually increased 92. At this stage, the quantifying test seeks to provoke a compensation pattern and then identify and quantify 94 the power level at the first sign of a compensation pattern. For instance, as the power level is increased 92 across the bicep-tricep muscles, the trainee's arm will begin to react visibly at the onset of the on duty cycle. One type of compensation pattern occurs as a twitch type of motion, wherein the forearm or hand moves forward or rearward from its rest position. This occurs because the trainee's tricep could not react fast enough to respond to the signal in the bicep, or vice versa. As the amount of visible twitch type motion increases, a further compensation pattern may become visible associated with another muscle from the group, such as a rotation of the wrist caused by the forearm muscles firing responsive to the stimulation on the bicep. The power level at which the compensation pattern starts is identified and recorded 94.

The same quantifying test procedure is repeated 96 for other opposing sets of muscles, one out of each group. That is, the same procedure can be repeated calves against anterior tibialis, quads against hamstrings, lats against pecs, etc. The objective for the quantifying test is to identify a hierarchy of communication of the muscles within each group. The highest performing muscle in each group is identified 84 as the facilitator muscle.

Once the facilitator muscle is identified 84, training continues using a set of protocols to teach 86 the other muscles in the group to neurologically communicate more like the facilitator muscle. One of each electrode pair (such as the black electrodes) are placed 98 on the facilitator muscle, with the body positioned 100 at the greatest joint angle for that muscle. For instance, if the triceps are identified as the facilitator muscle, the black electrodes are placed 98 on the triceps with the elbow joint extended 100. The opposite electrode out of each electrode pair (e.g., the red electrodes) are placed 98 on the receiver muscle.

The settings for the dual periodic-exponential signal are then adjusted 102 based upon the results of the quantification test and where the trainee is in his or her training. Namely, the power is set at the value recorded 92 when the trainee's compensation pattern began. A new trainee will use a ¼ on, 3 off duty cycle, a mid-range trainee will use a ¼ on 2 off duty cycle, and an advanced trainee will use a ¼ on, 1 off duty cycle. The power is then applied for a training duration both at low and at higher frequency 104, preferably at the quantification testing frequencies. During application 102 of the training signal, the trainee flexes and relaxes 106 the receiver muscle, moving the limb controlled by the receiver muscle. This process trains the receiver muscle to open its neurologic communication more like that of the facilitator muscle.

The training may proceed and be repeated 108 through multiple phases. For instance, a first phase of a standard training regimen would be 3 minutes, 1½ minutes at the low frequency (40 pps, or 10 pps if available) setting for the electro-therapeutic stimulator 10 followed 110 by 1½ minutes at the higher frequency (245 pps) setting for the electro-therapeutic stimulator 10. A second phase of a standard training regimen would be the same 90 second durations but using 40 pps followed 110 by 130 pps. A third phase of a standard training regimen would be the same 90 second durations but using 10 pps followed 110 by 130 pps. Throughout all phases 108 and both at low and mid-high frequencies 110, the objective of the training regimen is to elicit the greatest response in the receiver muscle, with the receiver muscle generating its cues by emulating the neurologic communication of the facilitator muscle.

For best performance of the training protocols, it is important that the stimulator 10 be able to quickly achieve full power and full depth of penetration, both of the main pulse 32 and the background pulse 30. Particularly for the main pulse 32, the duty cycle should proceed from fully off to fully on in a time period of one second or less. Even more preferably, the on portion of the duty cycle of the main pulse 32 is one second or less, with a preferred on duration of ¼ second. With full power and a full depth of penetration reached very quickly, the receiver muscle while flexing seems to identify more thoroughly with the neurologic signal from the facilitator muscle. The receiver muscle then emulates the performance of the receiver muscle more quickly and more thoroughly. The training as a whole increases the speed at which the receiver muscles can be fired responsive to a signal from the brain. Injuries and joint pain are avoided by building the ability of the muscles to absorb force.

Although the present invention has been described with reference to preferred embodiments, workers skilled in the art will recognize that changes may be made in form and detail without departing from the spirit and scope of the invention.

The invention claimed is:

1. A method of electro-therapeutic diagnosis to determine a location of cellular disruption in muscle tissue of a conscious living patient, comprising:
   transdermally applying an electric diagnosis signal by placement of at least a first electrode and a second electrode on the patient's skin, the electric diagnosis signal having a waveform comprising:
      a periodic-exponential background pulse at a frequency of 1 to 1000 kilohertz;
   moving the first electrode across the patient's skin while the second electrode is placed at a stationary anchor location, thereby locating a first cellular disruption end point where a sensation felt by the patient associated with the background pulse is maximized; and
   while the first electrode is at the first cellular disruption end point, moving the second electrode across the patient's skin, thereby locating an opposing cellular disruption end point where the sensation felt by the patient associated with the background pulse is maximized; and
   prior to applying the electric diagnosis signal, performing an electro-therapeutic adjustment across the patient's right and left hip flexors, wherein the electro-therapeutic adjustment comprises:
      placing first and second electrodes of a first electrode pair on the patient's skin, with the first electrode of the first electrode pair positioned on the patient's inner left thigh near a terminal end of the patient's left hip flexor and the second electrode of the first electrode pair positioned on the patient's back;
      placing first and second electrodes of a second electrode pair on the patient's skin, with the first electrode of the second electrode pair positioned on the patient's inner right thigh near a terminal end of the patient's right hip flexor and the second electrode of the second electrode pair positioned on the patient's back;

transdermally applying an electric adjustment signal across both electrode pairs, the electric adjustment signal comprising:
- a background pulse; and
- a main pulse having a power level which is controllable;

during application of the electric adjustment signal, having the patient perform repetitions of movements.

2. The method of claim 1, wherein the first periodic-exponential background pulse is at a frequency of 8 to 12 kilohertz.

3. The method of claim 1, wherein the first periodic-exponential background pulse is at a frequency of about 10 kilohertz.

4. The method of claim 1, wherein the first periodic-exponential background pulse has a power delivery pulse width of about 25 μs.

5. The method of claim 1, wherein the stationary anchor location is at the patient's waist adjacent the patient's lumbar triangle.

6. The method of claim 1, further comprising:
after locating the first cellular disruption end point and the opposing cellular disruption end point, applying an electro-therapeutic treatment across the cellular disruption end points.

7. The method of claim 1, wherein the repetitions of movements comprise:
during application of the electric adjustment signal, having the patient perform a cross-crawl pattern movement, comprising moving the patient's right arm and left leg simultaneously forward and back followed by moving the patient's left arm and right leg simultaneously forward and back.

8. The method of claim 7, wherein the power of the main pulse is applied at a power level of first sensation to the patient.

9. The method of claim 7, wherein the main pulse is a periodic-exponential signal applied at a frequency of 40 to 100 hertz.

10. The method of claim 7, wherein the background pulse of the electric adjustment signal is a periodic-exponential signal applied at a frequency of over 1 kilohertz.

11. The method of claim 1, comprising communicating with the patient to determine electrode locations where the sensation felt by the patient associated with the background pulse is maximized.

12. A method of electro-therapeutic diagnosis to determine a location of cellular disruption in muscle tissue of a conscious living patient, comprising:
transdermally applying an electric diagnosis signal by placement of at least a first electrode and a second electrode on the patient's skin, the electric diagnosis signal having a waveform comprising:
- a periodic-exponential background pulse at a frequency of 1 to 1000 kilohertz;

moving the first electrode across the patient's skin while the second electrode is placed at a stationary anchor location, thereby locating a first cellular disruption end point where a sensation felt by the patient associated with the background pulse is maximized; and while the first electrode is at the first cellular disruption end point, moving the second electrode across the patient's skin, thereby locating an opposing cellular disruption end point where the sensation felt by the patient associated with the background pulse is maximized;

and further comprising electro-therapeutic treatment to address pain in a movement, the electro-therapeutic treatment comprising:
transdermally applying an electric treatment signal comprising:
- a periodic-exponential background pulse at a frequency over 1 kilohertz; and
- a periodic-exponential main pulse at a frequency of 1 to 500 hertz;

adjusting power on the main pulse of the electric treatment signal to a threshold where the patient compensates in response to the electric treatment signal;

having the patient perform the movement associated with the pain being addressed for a number of repetitions while applying the electric treatment signal at the adjusted power;

increasing power on the main pulse of the electric treatment signal; and having the patient repeat the movement for a number of repetitions while applying the electric treatment signal at the increased power.

13. The method of claim 12, further comprising:
prior to applying the electric diagnosis signal, performing an electro-therapeutic adjustment across the patient's right and left hip flexors.

14. The method of claim 13, wherein the electro-therapeutic adjustment comprises:
placing first and second electrodes of a first electrode pair on the patient's skin, with the first electrode of the first electrode pair positioned on the patient's inner left thigh near a terminal end of the patient's left hip flexor and the second electrode of the first electrode pair positioned on the patient's back;

placing first and second electrodes of a second electrode pair on the patient's skin, with the first electrode of the second electrode pair positioned on the patient's inner right thigh near a terminal end of the patient's right hip flexor and the second electrode of the second electrode pair positioned on the patient's back;

transdermally applying an electric adjustment signal across both electrode pairs, the electric adjustment signal comprising:
- a background pulse; and
- a main pulse having a power level which is controllable;

during application of the electric adjustment signal, having the patient perform repetitions of movements.

15. The method of claim 14, wherein the repetitions of movements are repetitions of movements of the ankle joint.

16. The method of claim 15, wherein the main pulse is a periodic-exponential signal applied at a continuous power level for a duration of at least 30 seconds.

17. The method of claim 15, wherein the power of the main pulse is applied at a power level of first sensation to the patient.

18. The method of claim 15, wherein the main pulse is a periodic-exponential signal applied at a frequency of 40 to 100 hertz.

19. The method of claim 15, wherein the background pulse of the electric adjustment signal is a periodic-exponential signal applied at a frequency of over 1 kilohertz.

20. The method of electro-therapeutic diagnosis and treatment of claim 12, and further comprising electro-therapeutic training comprising:
identifying a facilitator muscle out of a communicating muscle group which has a higher level of neuro-muscular communication than receiver muscles within that communicating muscle group; and transdermally applying an electro-therapeutic training signal by at least one electrode pair, with a first electrode of the electrode pair placed on the facilitator muscle and a second electrode of the electrode pair placed on one receiver muscle, the electric training signal comprising:
  a periodic-exponential background pulse at a frequency over 1 kilohertz; and
  a periodic-exponential main pulse at a frequency of 1 to 500 hertz;

during application of the electric training signal, flexing the receiver muscles.

21. The method of claim 20, wherein the communicating muscle group is selected from:
  a first communicating muscle group consisting of the following muscles: calves (gastrocnemius and soleus), quads (quadriceps femoris), hip flexors (primarily the iliopsoas and adductors), lats (latissimus dorsi), biceps, forearms (brachioradialis), gluts (gluteus maximus), abdominals and lower back (primarily the thoracolumbar fascia); and
  a second muscle group consisting of the following muscles:
    anterior tibialis, hamstrings (biceps femoris), pecs (pectoralis major), triceps (triceps brachii), gluts (gluteus maximus), abdominals and lower back (primarily the thoracolumbar fascia).

22. The method of claim 20, wherein the act of identifying facilitator muscles comprises:
  electrically stimulating opposing muscles, and
  observing compensation patterns associated with the electrically stimulating the opposing muscles.

23. The method of claim 20, wherein electric training signal is applied with the joint of the facilitator muscle at an extended position.

24. The method of claim 20, wherein electric training signal is applied with a duty cycle that proceeds from fully off to fully on in one second or less.

* * * * *